US00PP31949P3

(12) United States Plant Patent
van den Haak

(10) Patent No.: US PP31,949 P3
(45) Date of Patent: Jul. 7, 2020

(54) *PHLOX* PLANT NAMED 'IFPHLFC'

(50) Latin Name: *Phlox paniculata*
Varietal Denomination: IFPHLFC

(71) Applicant: Jelle van den Haak, Amsterdam (NL)

(72) Inventor: Jelle van den Haak, Amsterdam (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 16/501,196

(22) Filed: Mar. 5, 2019

(65) Prior Publication Data

US 2020/0053937 P1 Feb. 13, 2020

Related U.S. Application Data

(60) Provisional application No. 62/764,553, filed on Aug. 7, 2018.

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
See application file for complete search history.

*Primary Examiner* — Susan McCormick Ewoldt
(74) *Attorney, Agent, or Firm* — C. A. Whealy

(57) ABSTRACT

A new and distinct cultivar of *Phlox* plant named 'IFPHLFC', characterized by its compact and uniformly mounded plant habit; moderately vigorous to vigorous growth habit; freely branching habit; dark green-colored leaves; freely flowering habit; flowers that are red to red purple and white bi-colored with red purple-colored throats; and good container and garden performance.

2 Drawing Sheets

Botanical designation: *Phlox paniculata.*
Cultivar denomination: 'IFPHLFC'.

CROSS-REFERENCED TO CLOSELY RELATED APPLICATIONS

Title: Varieties of *Phlox* Plants
Applicant: Jelle van den Haak
Provisional application Ser. No. 62/764,553
Filed: Aug. 7, 2018

BACKGROUND OF THE INVENTION

The present invention relates to a new and distinct cultivar of *Phlox* plant, botanically known as *Phlox paniculata*, typically grown as a container and garden *Phlox*, hereinafter referred to by the name 'IFPHLFC' and disclosed in U.S. Provisional Patent Application Ser. No. 62/764,553.

The new *Phlox* plant is a product of a planned breeding program conducted by the Inventor in Andijk, The Netherlands. The objective of the breeding program is to create new vigorous *Phlox* plants with numerous attractive flowers.

The new *Phlox* plant originated from a cross-pollination of a proprietary selection of *Phlox paniculata* identified as code number 047-12-K024-02, not patented, as the female, or seed, parent with a proprietary selection of *Phlox paniculata* identified as code number 9009-05, not patented, as the male, or pollen, parent in August, 2013. The new *Phlox* plant was discovered and selected as a single plant from within the progeny of the stated cross-pollination in a controlled nursery environment in Andijk, The Netherlands in August, 2014.

Asexual reproduction of the new *Phlox* plant by cuttings in a controlled environment in Andijk, The Netherlands since February, 2015 has shown that the unique features of this new *Phlox* plant are stable and reproduced true to type in successive generations.

SUMMARY OF THE INVENTION

The new *Phlox* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFPHLFC'. These characteristics in combination distinguish 'IFPHLFC' as a new and distinct *Phlox* plant:

1. Compact and uniformly mounded plant habit.
2. Moderately vigorous to vigorous growth habit.
3. Freely branching habit.
4. Dark green-colored leaves.
5. Freely flowering habit.
6. Flowers that are red to red purple and white bi-colored with red purple-colored throats.
7. Good container and garden performance.

Plants of the new *Phlox* and the female parent selection differ primarily in plant habit as plants of the female parent selection are more compact than plants of the female parent selection.

Plants of the new *Phlox* and the male parent selection differ primarily in the following characteristics:

1. Leaves of plants of the new *Phlox* are lighter green in color than leaves of plants of the male parent selection.
2. Plants of the new *Phlox* and the male parent selection differ in flower color as flowers of plants of the new *Phlox* are red to red purple and white bi-colored with red purple-colored throats whereas flowers of plants of the male parent selection are purple in color.

Plants of the new *Phlox* can also be compared to plants of *Phlox paniculata* 'Barsixtytwo', disclosed in U.S. Plant Pat. No. 22,234. In side-by-side comparisons, plants of the new *Phlox* and 'Barsixtytwo' differ in the following characteristics:

1. Plants of the new *Phlox* are more compact than plants of 'Barsixtytwo'.
2. Plants of the new *Phlox* are more freely branching than plants of 'Barsixtytwo'.
3. Plants of the new *Phlox* and 'Barsixtytwo' differ in flower color as flowers of plants of the new *Phlox* are red to red purple and white bi-colored with red purple-colored throats whereas flowers of plants 'Barsixtytwo' are coral red in color.

BRIEF DESCRIPTION OF THE PHOTOGRAPHS

The accompanying photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'IFPHLFC' grown in a container.

The photographs on the second sheet are close-up views of typical inflorescences (upper photograph) and typical leaves (lower photograph) of 'IFPHLFC'.

DETAILED BOTANICAL DESCRIPTION

The aforementioned photographs and following observations and measurements describe plants grown during the summer in 17-cm containers in an outdoor nursery in Heerhugowaard, The Netherlands and under cultural practices typically used in commercial *Phlox* production. During the production of the plants, day temperatures ranged from 10° C. to 25° C. and night temperatures ranged from 4° C. to 15° C. Plants were pinched five weeks after planting and were 15 weeks old when the photographs and description were taken. In the following description, color references are made to The Royal Horticultural Society Colour Chart, 2015 Edition, except where general terms of ordinary dictionary significance are used.

Botanical classification: *Phlox paniculata* 'IFPHLFC'.

Parentage:

*Female, or seed, parent.*—Proprietary selection of *Phlox paniculata* identified as code number 047-12-K024-02, not patented.

*Male, or pollen, parent.*—Proprietary selection of *Phlox paniculata* identified as code number 9009-05, not patented.

Propagation:

*Type.*—By terminal cuttings.

*Time to initiate roots, summer.*—About 12 days at temperatures about 20° C.

*Time to initiate roots, winter.*—About 16 days at temperatures about 20° C.

*Time to produce a rooted young plant, summer.*—About 36 days at temperatures about 18° C.

*Time to produce a rooted young plant, winter.*—About 42 days at temperatures about 18° C.

*Root description.*—Medium in thickness, moderately fibrous; close to 158B to 158C in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Herbaceous perennial; broadly upright and relatively compact plant habit; overall shape, broadly and short inverted triangle; moderately vigorous to vigorous in growth habit and moderate growth rate.

*Plant height, soil level to top of foliar plane.*—About 28 cm.

*Plant height, soil level to top of floral plane.*—About 34.4 cm.

*Plant width (spread).*—About 47.5 cm.

*Lateral branches.*—Quantity: About three primary branches and about twelve secondary branches per plant. Length: About 16.7 cm. Diameter: About 4 mm. Internode length: About 2.4 cm. Strength: Strong. Aspect: Upright to about 45° from vertical. Texture and luster: Smooth, glabrous; moderately glossy. Color: Close to 144A to 144B; at the petiole attachment, strongly tinged with close to N186C.

Leaf description:

*Arrangement.*—Opposite, simple.

*Length.*—About 10.4 cm.

*Width.*—About 4.2 cm.

*Shape.*—Elliptic to ovate; moderately carinate.

*Apex.*—Apiculate.

*Base.*—Truncate.

*Margin.*—Entire; very finely serrate, serrations are inconspicious.

*Texture and luster, upper surface.*—Smooth, glabrous; slightly rugose; slightly glossy.

*Texture and luster, lower surface.*—Smooth, glabrous; slightly rugose; matte.

*Venation pattern.*—Pinnate.

*Color.*—Developing leaves, upper surface: Close to 137C. Developing leaves, lower surface: Close to 138B. Fully expanded leaves, upper surface: Close to NN137A; venation, close to N144A. Fully expanded leaves, lower surface: Close to 191A; venation, close to 144C.

*Petioles.*—Length: About 3 mm. Diameter: About 2.5 mm by 3 mm. Texture and luster, upper and lower surfaces: Smooth, glabrous; matte. Color, upper surface: Close to 144C; proximally, tinged with close to N186C. Color, lower surface: Close to 144C.

Flower description:

*Flower type and flowering habit.*—Single rotate and salverform flowers arranged in compound terminal panicles; flowers face upright to outwardly; panicles roughly hemispherical in shape; freely flowering habit with about 450 flowers developing per inflorescence and about 4,000 flowers developing per plant during the flowering season.

*Fragrance.*—Moderately fragrant; sweet, pleasant.

*Natural flowering season.*—Plants begin flowering about 15 weeks after planting; long flowering period, plants flower continuously throughout the summer in The Netherlands.

*Flower longevity.*—Flowers last about ten days on the plant; flowers not persistent.

*Flower buds.*—Height: About 2 cm. Diameter: About 5 mm. Shape: Oblanceolate. Texture and luster: Smooth, glabrous; slightly glossy. Color: Close to 68A; tube, between 59B and 61A; developing calyx, close to 145A to 145B with axillary stripes, close to N199B.

*Inflorescence height.*—About 16 cm.

*Inflorescence diameter.*—About 17 cm.

*Flower diameter.*—About 2.5 cm.

*Flower depth.*—About 2 cm.

*Flower throat diameter.*—About 4 mm.

*Flower tube length.*—About 1.7 cm.

*Flower tube diameter.*—About 3 mm.

*Petals.*—Quantity per flower: Typically five in a single whorl; petals fused at the base into a narrow tube; free parts moderately imbricate. Length (including tube): About 2.9 cm; 62.5% of the petal is fused. Lobe width: About 1.4 cm. Lobe shape: Spatulate. Lobe apex: Obtuse. Margin: Entire; slightly to moderately undulate. Texture and luster, upper surface: Smooth, glabrous; moderately velvety; matte. Texture and luster, lower surface: Smooth, glabrous; slightly glossy. Texture, throat: Smooth, glabrous; moderately velvety. Texture, tube: Moderately pubescent. Color: When opening, upper surface: Close to 52A; towards the throat, close to NN155D. When opening, lower surface: Close to 52B to 52D flushed with close to 72B and NN155D. Fully opened, upper surface: Close to 58C; towards the throat, close to N155A; venation, similar to lamina colors; color does not change with development. Fully opened, lower surface: Close to 58D flushed with close to 77B and NN155D; venation, similar to lamina colors; color does not change with development. Throat: Close to 64B; venation, close to 64B. Tube: Close to N80A; venation, close to N80A.

*Sepals.*—Quantity per flower: Typically five in a single whorl, fused towards the base; calyx, campanulate. Length: About 9 mm; 43% of the sepal is fused. Width: About 1.5 mm. Shape: Lanceolate. Apex: Narrowly apiculate. Margin: Entire; not undulate. Texture and luster, upper and lower surfaces: Smooth, glabrous; slightly glossy. Color: When opening, upper and lower surfaces: Close to 145A to 145B; axillary stripes, close to N199B; towards the margins, close to 145D. Fully opened, upper and lower surfaces: Close to 145C; axillary stripes, close to N199B; towards the margins, close to 145D; venation, close to N199B.

*Peduncles.*—Length, terminal peduncles: About 13 cm. Diameter, terminal peduncles: About 2.5 mm. Aspect, primary peduncles: Erect. Aspect, secondary peduncles: About 45° from vertical. Strength: Strong. Texture and luster: Smooth, glabrous; moderately glossy. Color: Between 143B and 144A.

*Pedicels.*—Length: About 8 mm. Diameter: About 1 mm. Angle: About 20° from the peduncle axis. Strength: Moderately strong. Texture and luster: Densely pubescent; moderately glossy. Color: Close to 143B.

*Reproductive organs.*—Stamens: Quantity per flower: Typically five. Filament length: About 1 mm. Filament color: Close to N155A. Anther size: About 1.5 mm by 1 mm. Anther shape: Narrowly oblong. Anther color: Close to 159D. Pollen amount: Scarce. Pollen color: Close to 160B. Pistils: Quantity per flower: One. Pistil length: About 1.2 cm. Style length: About 1 cm. Style color: Close to 182C; proximally, close to 145B. Stigma size: About 1.5 mm by 1.5 mm. Stigma shape: Cleft, three-parted. Stigma color: Close to 150D. Ovary color: Close to 143C.

*Seeds and fruits.*—To date, seed and fruit development have not been observed on plants of the new *Phlox*.

Garden performance: Plants of the new *Phlox* have been observed to have good garden performance and tolerate rain, wind, high temperatures about 35° C. and to be suitable for USDA Hardiness. Zones 6 through 10.

Pathogen & pest resistance: Plants of the new *Phlox* have been not been observed to be resistant to pathogens and pests common to *Phlox* plants.

It is claimed:

1. A new and distinct *Phlox* plant named 'IFPHLFC' as illustrated and described.

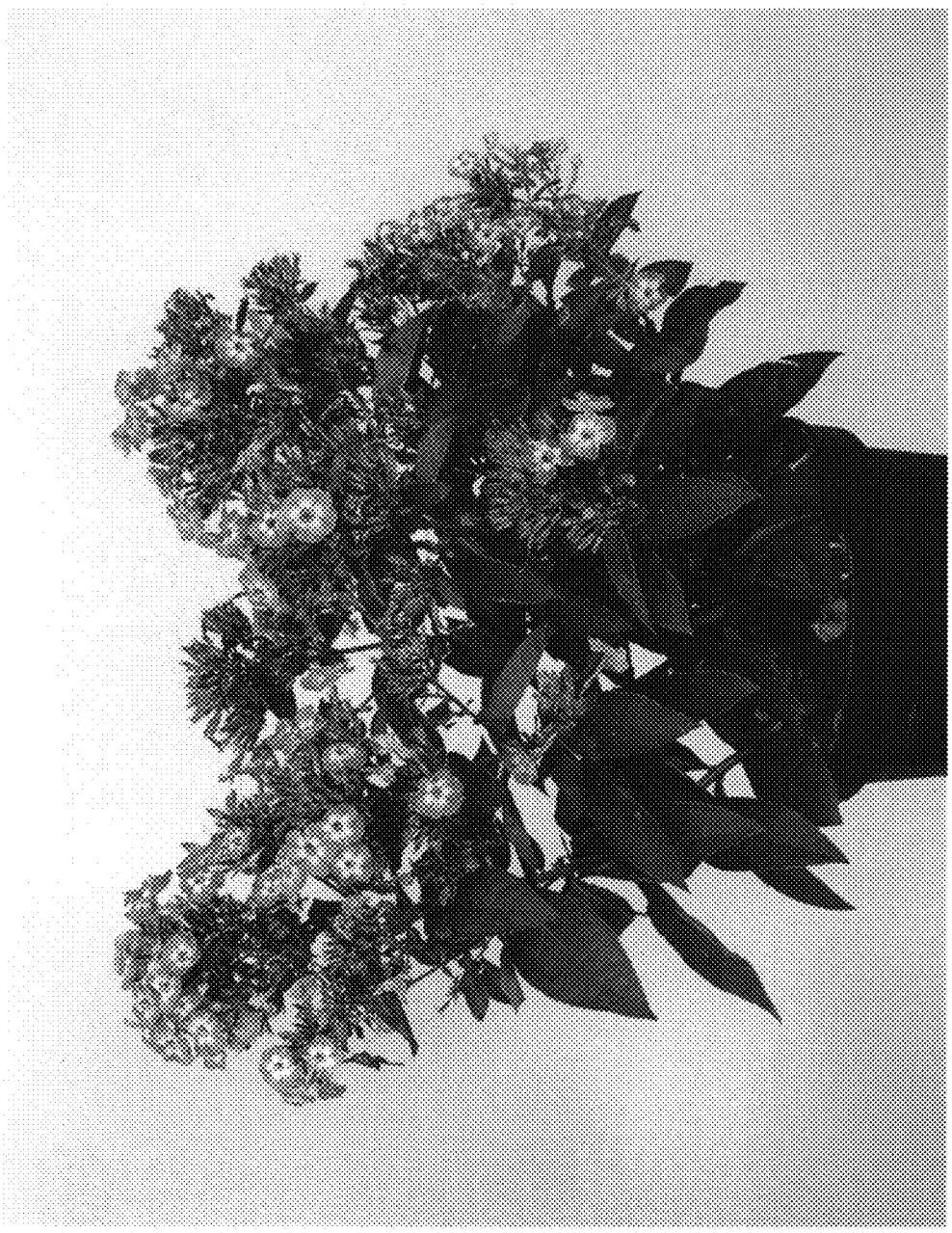

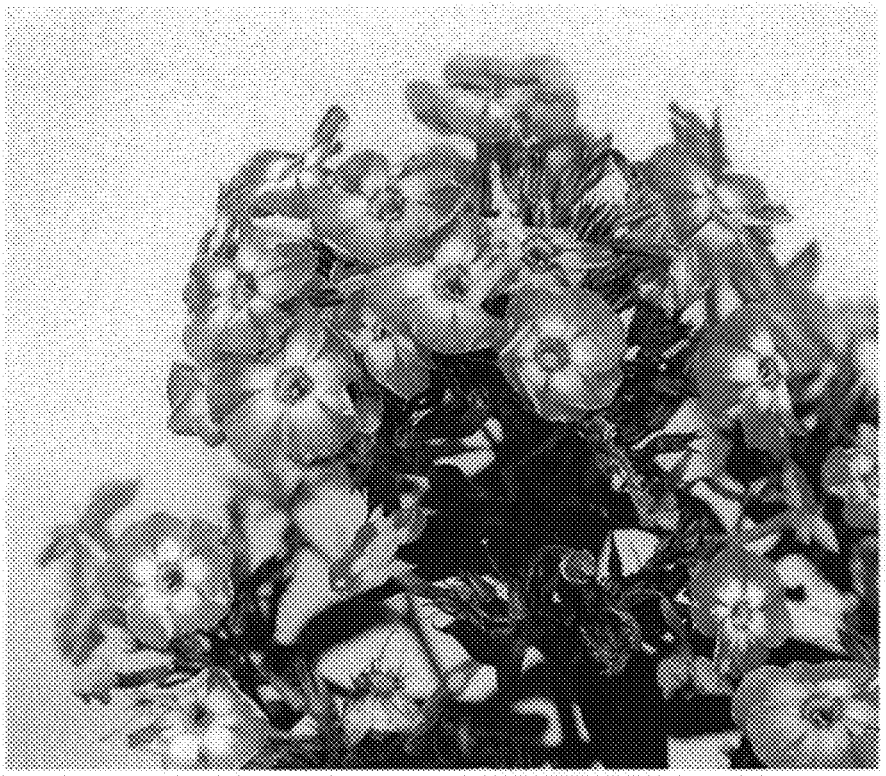
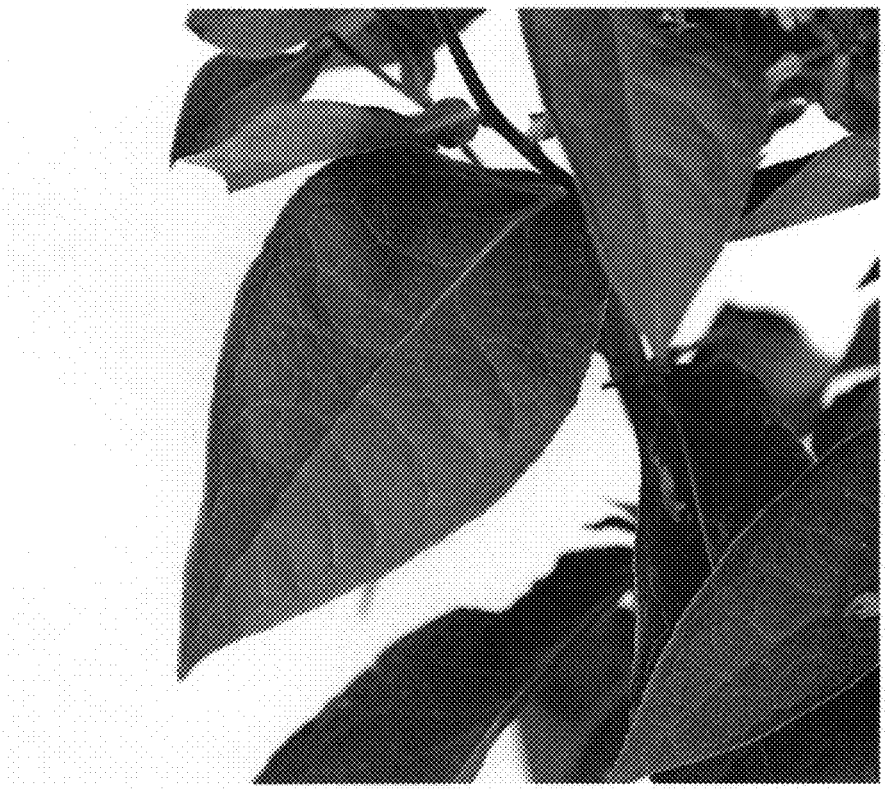

* * * * *